United States Patent
Shibayama et al.

(10) Patent No.: US 7,282,597 B2
(45) Date of Patent: Oct. 16, 2007

(54) ASCORBIC ACID DERIVATIVES AND SKIN-WHITENING COSMETICS

(75) Inventors: Hiroharu Shibayama, Osaka (JP); Koichi Ueda, Osaka (JP); Hachiro Indo, Osaka (JP); Satoshi Tachibana, Wakayama (JP); Hiroshi Nishikawa, Wakayama (JP); Masaru Yamabe, Wakayama (JP)

(73) Assignees: Toyo Beauty Co., Ltd., Osaka (JP); Sugai Chemical Industry Co., Ltd., Wakayama (JP)

( * ) Notice: Subject to any disclaimer, the term of this patent is extended or adjusted under 35 U.S.C. 154(b) by 0 days.

(21) Appl. No.: 10/554,872

(22) PCT Filed: Mar. 25, 2005

(86) PCT No.: PCT/JP2005/005532

§ 371 (c)(1),
(2), (4) Date: Oct. 31, 2005

(87) PCT Pub. No.: WO2005/092905

PCT Pub. Date: Oct. 6, 2005

(65) Prior Publication Data

US 2006/0264407 A1 Nov. 23, 2006

(30) Foreign Application Priority Data

Mar. 25, 2004 (JP) ............................. 2004-089876
Mar. 25, 2004 (JP) ............................. 2004-089893

(51) Int. Cl.
*C07D 305/12* (2006.01)
*C07F 9/06* (2006.01)

(52) U.S. Cl. ...................................... 549/315; 549/222

(58) Field of Classification Search ................ 549/222, 549/216, 315

See application file for complete search history.

(56) References Cited

U.S. PATENT DOCUMENTS

| 4,939,128 A | * | 7/1990 | Kato et al. ..................... 514/82 |
| 5,607,968 A | * | 3/1997 | Ptchelintsev ................ 514/474 |
| 5,780,504 A | * | 7/1998 | Ptchelintsev ................ 514/474 |
| 5,916,915 A | | 6/1999 | Hong et al. |

FOREIGN PATENT DOCUMENTS

| EP | 0 339 486 | 11/1989 |
| EP | 0 875 514 | 11/1998 |
| JP | 45-23634 | 8/1970 |
| JP | 52-18191 | 5/1977 |
| JP | 59-170085 | 9/1984 |
| JP | 03-139288 | 6/1991 |
| JP | 10-298174 | 11/1998 |
| JP | 2003-238386 | * 2/2002 |
| KR | 1999-000239 | 1/1999 |
| WO | 03/086384 | 10/2003 |

* cited by examiner

*Primary Examiner*—D. Margaret Seaman
*Assistant Examiner*—Nizal S. Chandrakumar
(74) *Attorney, Agent, or Firm*—Wenderoth, Lind & Ponack, L.L.P.

(57) ABSTRACT

It is an object to provide an L-ascorbic acid derivative which can keep the L-ascorbic acid stable to heat and light and thus has a long shelf life, which is high in permeability into the skin, which can be quickly hydrolyzed by phosphatase, an enzyme that is ubiquitous in vivo, and which exhibits physiological activities that are inherent to L-ascorbic acid and beneficial to health, a method for producing such an L-ascorbic acid derivative, and a skin-whitening cosmetic material.

There is provided an ascorbic acid derivative comprising an L-ascorbic acid-2-phosphate ester or a salt thereof wherein the phosphate ester has a branched alkyl group, the L-ascorbic acid-2-phosphate ester being of formula [13]. The ascorbic acid derivative is produced by a method comprising reacting a branched alkanol with phosphorus oxychloride to synthesize monoalkyldichlorophosphate or dialkylmonochlorophosphate, reacting the thus obtained substance with 5,6-O-isopropylidene-L-ascorbic acid obtained by reacting L-ascorbic acid with acetone, and subjecting the thus obtained substance to acid hydrolysis. There is also provided a cosmetic material containing such an ascorbic acid derivative by 0.05 to 80 percent by weight.

[13]

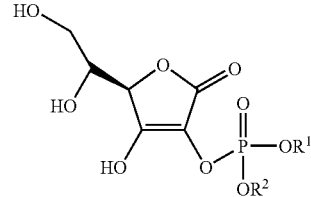

(wherein each of $R^1$ and $R^2$ is a hydrogen (H) atom or an alkyl group having branches and including 3 to 30 carbon atoms, but not both of $R^1$ and $R^2$ are hydrogen (H) atoms).

4 Claims, 2 Drawing Sheets

ASCORBIC ACID DERIVATIVES AND SKIN-WHITENING COSMETICS

TECHNICAL FIELD

This invention relates to ascorbic acid derivatives that are useful as cosmetics and quasi drugs used for whitening human skin, a method for manufacturing the same, and skin-whitening cosmetics.

BACKGROUND ART

It is generally known that L-ascorbic acid (vitamin C) has, besides the function of inhibiting lipid peroxides, the functions of promoting the production of collagen and strengthening the immune system, the functions of inhibiting the synthesis of melanin under the skin and reducing and fading any black melanin that has been synthesized. Thus, L-ascorbic acid is a well-known component of skin-whitening cosmetics that can inhibit the synthesis and/or reduce synthesized melanin, thereby inhibiting "spots" and "freckles".

L-ascorbic acid is extremely unstable to heat or oxidation and tend to become inert or decompose when heated or oxidized. This may make it difficult for L-ascorbic acid to fully exhibit its expected physiological function.

In order to prevent L-ascorbic acid from becoming unstable, there are known a derivative in which the diol portion of L-ascorbic acid, which is prone to oxidation, is subjected to phosphate esterification (Patent publication 1), and a derivative in which the diol portion is subjected to glycosidation (Patent publication 2).

But because these L-ascorbic acid derivatives are high in hydrophilicity, they are low in permeability into the skin.

In order to improve permeability of L-ascorbic acid into the skin, there are known an L-ascorbic acid derivative in which position 6 of L-ascorbic acid is acylated (Patent document 3), and a derivative in which position 4 of L-ascorbic acid is acylated (Patent document 4).

An L-ascorbic acid derivative is also known which shows both superior stability and permeability into the skin by acylating position 6 of L-ascorbic acid and further subjecting position 2 to phosphate esterification (Patent publication 5).

Patent document 1: JP patent publication 52-18191B
Patent document 2: JP patent publication 03-139288A
Patent document 3: JP patent publication 59-170085A
Patent document 4: JP patent publication 45-23634B
Patent document 5: JP patent publication 10-298174A

DISCLOSURE OF THE INVENTION

Problems to which the Invention Seeks a Solution

However, the derivative in which position 6 of L-ascorbic acid is acyl-esterified with fatty acid is not sufficient in chronological stability to heat and light during storage. The derivative in which position 2 is acyl-esterified with fatty acid cannot be quickly or sufficiently converted to L-ascorbic acid in the skin because no sufficient amount of esterase or lipase is present in the skin.

The derivative in which position 6 of L-ascorbic acid is acyl-esterified and position 2 is subjected to phosphate esterification cannot also be sufficiently converted to L-ascorbic acid in the skin because no sufficient amount of esterase or lipase is present in the skin.

Therefore, it is an object of the present invention to provide a novel L-ascorbic acid derivative which can keep the L-ascorbic acid stable to heat and light and thus has a long shelf life, which is high in permeability into the skin, which can be quickly hydrolyzed by phosphatase, a substance that is ubiquitous in vivo, and which exhibits physiological activities that are inherent to L-ascorbic acid and beneficial to health, and a method for producing such an L-ascorbic acid derivative.

Another object of the present invention is to provide a skin-whitening cosmetic material which can keep the L-ascorbic acid stable to heat and light and thus has a long shelf life, which is high in permeability into the skin, which can be quickly decomposed by enzymes that are ubiquitous in vivo, and which exhibits physiological activities that are inherent to L-ascorbic acid and beneficial in whitening the skin.

Means to Solve the Problems

According to the present invention, there is provided an ascorbic acid derivative comprising an L-ascorbic acid-2-phosphate ester or a salt thereof wherein the phosphate ester has a branched alkyl group, the L-ascorbic acid-2-phosphate ester being of formula [5]

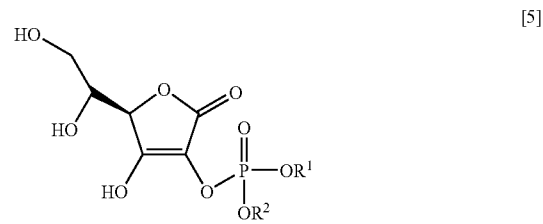

[5]

(wherein each of $R^1$ and $R^2$ is a hydrogen (H) atom or an alkyl group having branches and including 3 to 30 carbon atoms, but not both of $R^1$ and $R^2$ are hydrogen (H) atoms).

The phosphate ester, which is located at position 2 of the ascorbic acid derivative and has the branched alkyl group, provides suitable oil solubility to the derivative, thereby allowing the derivative to be easily absorbed into cells.

Except the phosphate alkyl ester portion, the ascorbic acid derivative according to the present invention is not modified at all, so that once it permeates into the skin, even without esterase or lipase, the derivative is hydrolyzed into L-ascorbic acid (vitamin C), phospholipids, etc. by enzymes such as phosphatase, which is ubiquitous in vivo. The derivative has thus a beneficial influence on the body.

The branched alkyl group is typically 2-heptylundecyl group, 2-octyldecyl group, 2-octyldodecyl group, 2-hexyldecyl group, 2-hexyl-dodecyl group, 2-isoheptylisoundecyl group, 16-methylheptadecyl group or 2-(1,3,3-trimethyl-n-butyl)-5,7,7-trimethyl-n-octyl group.

If the derivative is a salt, it is preferably a sodium salt, potassium salt, magnesium salt or calcium salt of L-ascorbic acid-2-phosphate ester.

The ascorbic acid derivative may be produced by a process comprising reacting a branched alkanol of formula [6] with phosphorus oxychloride to synthesize monoalkyldichlorophosphate of formula [7] or dialkylmonochlorophosphate of formula [8], reacting the thus obtained substance with 5,6-O-isopropylidene-L-ascorbic acid obtained by reacting L-ascorbic acid with acetone, and subjecting the thus obtained substance to acid hydrolysis.

R—OH  [6]

(wherein R is an alkyl group having branches and including 3 to 30 carbon atoms)

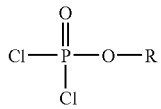  [7]

(wherein R is an alkyl group having branches and including 3 to 30 carbon atoms)

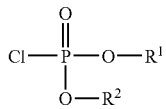  [8]

(wherein each of $R^1$ and $R^2$ is a hydrogen (H) atom or an alkyl group having branches and including 3 to 30 carbon atoms, but not both of $R^1$ and $R^2$ are hydrogen (H) atoms).

In order to solve the problems of conventional skin-whitening cosmetics, there is provided a skin-whitening cosmetic material containing an ascorbic acid derivative comprising an L-ascorbic acid-2-phosphate ester or a salt thereof wherein the phosphate ester has a branched alkyl group, the L-ascorbic acid-2-phosphate ester being of formula [5].

The phosphate ester, which is located at position 2 of the ascorbic acid derivative and has the branched alkyl group, provides suitable oil solubility to the derivative, thereby allowing the derivative to be easily absorbed into cells.

Except the phosphate alkyl ester portion, the ascorbic acid derivative according to the present invention is not modified at all, so that once it permeates into the skin, even without esterase or lipase, the derivative is hydrolyzed into L-ascorbic acid (vitamin C), phospholipids, etc. by enzymes such as phosphatase, which is ubiquitous in vivo. The derivative can thus whiten the skin.

In order for the skin-whitening cosmetic material according to the present invention to fully exhibit its skin-whitening effect, the content of the L-ascorbic acid-2-phosphate ester or its salt that are contained in the cosmetic material is preferably 0.05 to 80 percent by weight.

The skin-whitening cosmetic material has preferably a pH value of 4.0 to 9.0 in order to stabilize the ascorbic acid derivative, thereby allowing the ascorbic acid derivative to fully exhibit the expected effect.

ADVANTAGES OF THE INVENTION

Since the L-ascorbic acid according to the present invention is an L-ascorbic acid-2-phosphate ester or its salt of which the phosphate ester has a branched alkyl group, the L-ascorbic acid, which is otherwise unstable to heat and oxidation, stabilizes. Thus, it is possible to inhibit decomposition of the L-ascorbic acid during storage before use. During use, the ascorbic acid derivative according to the present invention is quickly decomposed into L-ascorbic acid, phospholipids, etc. by phosphatase, which is ubiquitous in vivo. Thus, the ascorbic acid derivative according to the present invention exhibits physiological activities that are inherent to L-ascorbic acid and beneficial to health.

The skin-whitening cosmetic material according to the present invention contains as its active ingredient L-ascorbic acid comprising an L-ascorbic acid-2-phosphate ester of which the phosphate ester has a branched alkyl group or its salt. Thus, the L-ascorbic acid becomes stable to heat and oxidation, so that the L-ascorbic acid is less likely to decomposed during storage before use. During use, the cosmetic material according to the present invention is quickly decomposed into L-ascorbic acid, phospholipids, etc. by enzymes that are ubiquitous in the skin such as phosphatase, so that the cosmetic material according to the invention exhibits physiological activities that are inherent to L-ascorbic acid and beneficial in whitening the skin. For example, the cosmetic material according to the present invention prevents "spots" and "freckles". By adjusting the pH value within the predetermined range, the ascorbic acid derivative will exhibits the expected function more effectively.

BEST MODE FOR EMBODYING THE INVENTION

Figure 1:
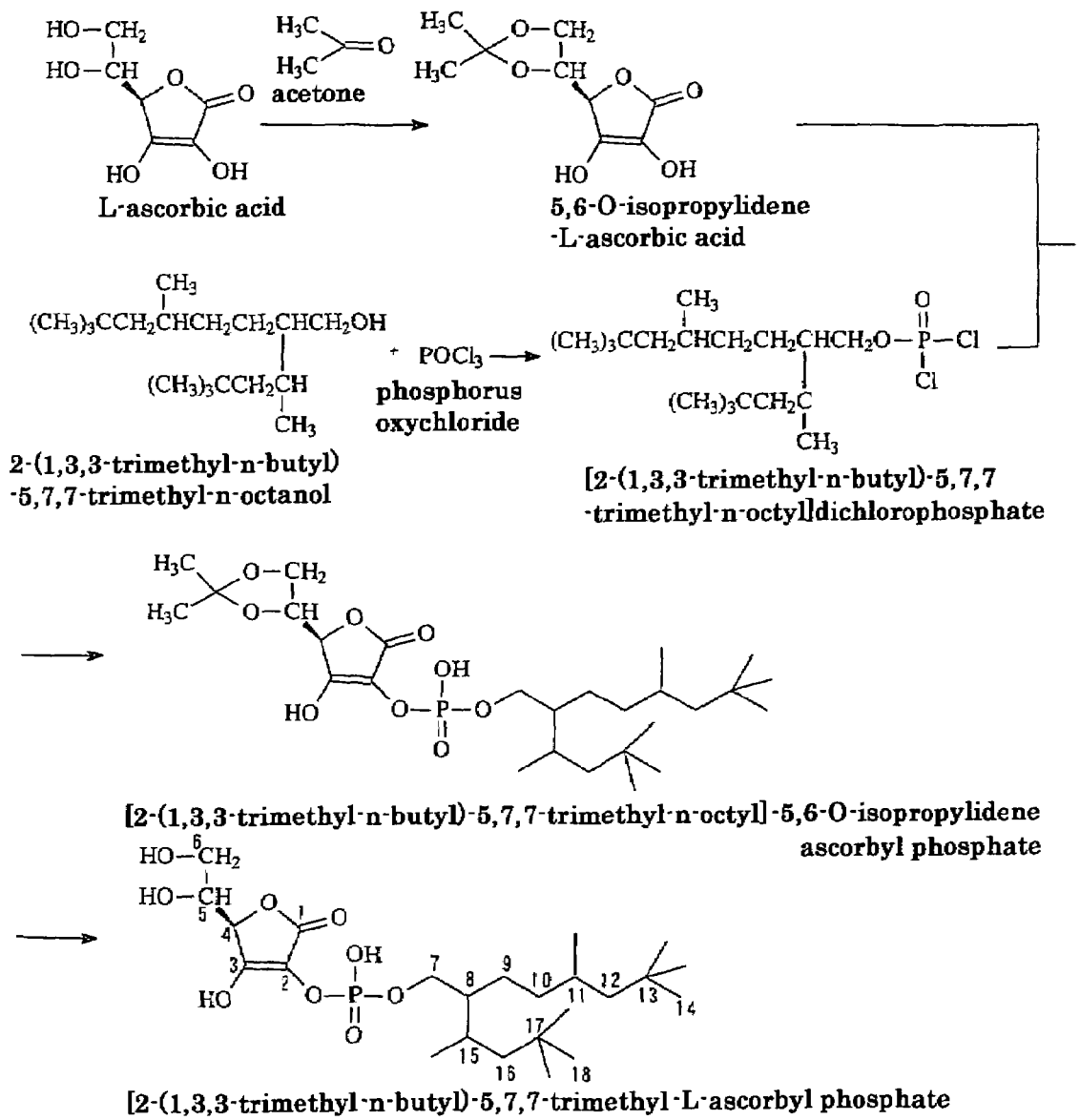
FIG. 1 shows the process for producing the ascorbic acid derivative of Example 1, using reaction formulas.

The L-ascorbic acid-2-phosphate ester of formula [5], i.e. 2-(branched alkyl)-L-ascorbyl phosphate is produced as follows:

First, using a nonpolar solvent selected from toluene, chlorobenzene, dichlorobenzene, etc., a branched alkanol of formula [6] is reacted with phosphorus oxychloride at −20 to 20 degrees Celsius in the presence of a base selected from trimethylamine, triethylamine, N,N-dimethylaniline, etc. to produce a monoalkyldichlorophosphate of formula [7] or a dialkyl-monochlorophosphate of formula [8]. The thus produced substance may be supplied to the next step after being isolated by distillation or in the form of a solution in the nonpolar solvent.

In the next step, the thus produced monoalkyldichlorophosphate or dialkylmonochlorophosphate is reacted with 5,6-O-isopropylidene-L-ascorbic acid obtained by reacting L-ascorbic acid with acetone, and the reaction product is hydrolyzed by acid and purified by a conventional method to produce the L-ascorbic acid-2-phosphate ester of formula [5].

Branched alkanols of formula [6] include 2-methyldecanol, 2-ethyldecanol, 2-propyldecanol, 2-butyldecanol, 2-pentyldecanol, 2-hexyldecanol, 2-heptyldecanol, 2-octyldecanol, 2-nonyldecanol, 2-methyl-undecanol, 2-ethylundecanol, 2-propylundecanol, 2-butylundecanol, 2-pentylundecanol, 2-hexylundecanol, 2-heptylundecanol, 2-octylundecanol, 2-nonylundecanol, 2-decylundecanol, 2-methyldodecanol, 2-ethyldodecanol, 2-propyldodecanol, 2-butyldodecanol, 2-pentyldodecanol, 2-hexyldodecanol, 2-heptyldodecanol, 2-octyldodecanol, 2-nonyldodecanol, 2-decyldodecanol, 2-undecyldodecanol and 2-isoheptylisoundecanol, and also include alkanols having branches at positions other than position 2, such as 16-methylheptadecanol and 2-(1,3,3-trimethyl-n-butyl)-5,7,7-trimethyl-n-octanol.

5,6-O-isopropylidene-L-ascorbic acid is produced by reacting L-ascorbic acid with acetone in the presence of a dehydrating agent such as acetyl chloride or fuming sulfuric acid at −30 to 20 degrees Celsius, and isolating it by e.g. filtering.

In the next step, using a nonpolar solvent selected from toluene, chlorobenzene, dichlorobenzene, etc., the thus obtained 5,6-O-isopropylidene-L-ascorbic acid is reacted with monoalkyldichlorophosphate of formula [7] or dialkylmonochlorophosphate of formula [8] at −20 to 20 degrees Celsius in the presence of a base selected from trimethylamine, triethylamine, N,N-dimethylaniline, etc., and the thus obtained substance is hydrolyzed by an acid selected from hydrochloric acid, sulfuric acid, acetic acid, etc. at −10 to 50 degrees Celsius.

During this step, in order to remove any remaining base, the substance is washed with an acid such as hydrochloric acid, sulfuric acid or acetic acid or an aqueous solution of an inorganic salt such as sodium chloride, potassium chloride, ammonium chloride, sodium carbonate, potassium carbonate or sodium hydrogen carbonate, and the nonpolar solvent is removed by evaporation. If higher quality is desired, 2-(branched alkyl)-L-ascorbyl phosphate of formula [5] is isolated by column chromatography. Alternatively, it may be supplied to the next step in the form of an ethanol or glycerol solution. Thus, the ascorbic acid derivative according to the present invention can be isolated and purified by any ordinary method.

Specific compounds of the ascorbic acid derivative of formula [5] according to the present invention include 2-(2-methyldecyl)-L-ascorbyl phosphate, 2-(2-ethyldecyl)-L-ascorbyl phosphate, 2-(2-propyldecyl)-L-ascorbyl phosphate, 2-(2-butyldecyl)-L-ascorbyl phosphate, 2-(2-pentyldecyl)-L-ascorbyl phosphate, 2-(2-hexyldecyl)-L-ascorbyl phosphate, 2-(2-heptyldecyl)-L-ascorbyl phosphate, 2-(2-octyldecyl)-L-ascorbyl phosphate, 2-(2-nonyldecyl)-L-ascorbyl phosphate, 2-(2-methylundecyl)-L-ascorbyl phosphate, 2-(2-ethylundecyl)-L-ascorbyl phosphate, 2-(2-propylundecyl)-L-ascorbyl phosphate, 2-(2-butylundecyl)-L-ascorbyl phosphate, 2-(2-pentylundecyl)-L-ascorbyl phosphate, 2-(2-hexylundecyl)-L-ascorbyl phosphate, 2-(2-heptylundecyl)-L-ascorbyl phosphate, 2-(2-octylundecyl)-L-ascorbyl phosphate, 2-(2-nonylundecyl)-L-ascorbyl phosphate, 2-(2-decylundecyl)-L-ascorbyl phosphate, 2-(2-methyldodecyl)-L-ascorbyl phosphate, 2-(2-ethyldodecyl)-L-ascorbyl phosphate, 2-(2-propyldodecyl)-L-ascorbyl phosphate, 2-(2-butyldodecyl)-L-ascorbyl phosphate, 2-(2-pentyldodecyl)-L-ascorbyl phosphate, 2-(2-hexyldodecyl)-L-ascorbyl phosphate, 2-(2-heptyldodecyl)-L-ascorbyl phosphate, 2-(2-octyldodecyl)-L-ascorbyl phosphate, 2-(2-nonyldodecyl)-L-ascorbyl phosphate, 2-(2-decyldodecyl)-L-ascorbyl phosphate, 2-(2-undecyldodecyl)-L-ascorbyl phosphate, 2-(2-isoheptyl-isoundecyl)-L-ascorbyl phosphate, 2-(16-methylheptadecyl)-L-ascorbyl phosphate, 2-bis(2-methyldecyl)-L-ascorbyl phosphate, 2-bis(2-ethyldecyl)-L-ascorbyl phosphate, 2-bis(2-propyldecyl)-L-ascorbyl phosphate, 2-bis(2-butyldecyl)-L-ascorbyl phosphate, 2-bis(2-pentyldecyl)-L-ascorbyl phosphate, 2-bis(2-hexyldecyl)-L-ascorbyl phosphate, 2-bis(2-heptyldecyl)-L-ascorbyl phosphate, 2-bis(2-octyldecyl)-L-ascorbyl phosphate, 2-bis(2-nonyldecyl)-L-ascorbyl phosphate, 2-bis(2-methylundecyl)-L-ascorbyl phosphate, 2-bis(2-ethylundecyl)-L-ascorbyl phosphate, 2-bis(2-propylundecyl)-L-ascorbyl phosphate, 2-bis(2-butylundecyl)-L-ascorbyl phosphate, 2-bis(2-pentylundecyl)-L-ascorbyl phosphate, 2-bis(2-hexylundecyl)-L-ascorbyl phosphate, 2-bis(2-heptylundecyl)-L-ascorbyl phosphate, 2-bis(2-octylundecyl)-L-ascorbyl phosphate, 2-bis(2-nonylundecyl)-L-ascorbyl phosphate, 2-bis(2-decylundecyl)-L-ascorbyl phosphate, 2-bis(2-methyldodecyl)-L-ascorbyl phosphate, 2-bis(2-ethyldodecyl)-L-ascorbyl phosphate, 2-bis(2-propyldodecyl)-L-ascorbyl phosphate, 2-bis(2-butyldodecyl)-L-ascorbyl phosphate, 2-bis(2-pentyldodecyl)-L-ascorbyl phosphate, 2-bis(2-hexyldodecyl)-L-ascorbyl phosphate, 2-bis(2-heptyldodecyl)-L-ascorbyl phosphate, 2-bis(2-octyldodecyl)-L-ascorbyl phosphate, 2-bis(2-nonyldodecyl)-L-ascorbyl phosphate, 2-bis(2-decyldodecyl)-L-ascorbyl phosphate, 2-bis(2-undecyldodecyl)-L-ascorbyl phosphate, 2-bis(2-isoheptylisoundecyl)-L-ascorbyl phosphate, 2-bis(16-methylheptadecyl)-L-ascorbyl phosphate, and 2-bis[2-(1,3,3-trimethyl-n-butyl)-5,7,7-trimethyl-n-octyl]-L-ascorbyl phosphate. The abovementioned compounds all include alkyl groups branched at position 2. But needless to say, the ascorbic acid derivative according to the present invention may be one including an alkyl group branched at a position other than position 2, such as 2-[2-(1,3,3-trimethyl-n-butyl)-5,7,7-trimethyl-n-octyl]-L-ascorbyl phosphate.

The ascorbic acid derivative according to the present invention may be replaced with one of salts thereof including alkali metal salts such as sodium salts and potassium salts, alkali earth metal salts such as calcium salts and magnesium salts, basic amino acids such as arginine, and organic amines such as triethanolamine.

In order for the skin-whitening cosmetic material according to the present invention to fully reveal its skin-whitening function, it preferably contains such L-ascorbic acid-2-phosphate ester or its salt in an amount of 0.05 to 80 percent by weight. If its content is less than 0.05 percent by weight, the cosmetic material will not reveal its skin-whitening function at all or reliably. If its content exceeds 80 percent by weight, the cosmetic material may not give good feelings to the user when applied to the skin. Thus, more preferably, the cosmetic material contains the above substance in an amount of 2 to 50 percent by weight.

The pH value of the skin-whitening cosmetic material according to the present invention is not particularly limited. But preferably, the cosmetic material according to the invention has a pH value of 4.0 to 9.0 to improve stability during storage. Outside this range, the ester tends to hydrolyze, thus destabilizing the cosmetic material.

Besides the abovementioned essential components, the skin-whitening cosmetic material according to the present invention may contain components used in ordinary cosmetics, drugs and quasi drugs, such as oil components, emulsifiers, humectants, thickeners, active drug components, preservatives, pigments, powders, pH adjusters, UV absorbers, antioxidants and perfumes.

Specific oil components include liquid paraffin, Vaseline, microcrystalline wax, squalane, jojoba oil, beeswax, carnauba wax, lanoline, olive oil, coconut oil, higher alcohols, fatty acids, esters of higher alcohols and fatty acids and silicone oil. Specific emulsifiers include nonionic surfactants such as polyoxyethylene alkyl ether, polyoxyethylene fatty ester, polyoxyethylene sorbitan fatty ester, sorbitan fatty ester, glycerin fatty ester, polyglycerin fatty ester and polyoxyethylene hydrogenated castor oil, anionic surfactants such as sodium stearoyl lactate, amphoteric surfactants such as soy phospholipid, and cationic surfactants such as alkyltrimethyl ammonium chloride. Specific humectants include glycerin, sorbitol, xylitol, maltitol, propylene glycol, polyethylene glycol, 1,3-butylene glycol, and 1,2-pentanediol. Specific thickeners include carboxyvinyl polymer, xanthan gum, methylcellulose, polyvinyl pyrolidone, gelatin and clay minerals such as bentonite. Specific active drug components include vitamins, their derivatives, allantoin, glycyrrhetinic acid and its derivatives, and animal and vegetable extracts.

The skin-whitening cosmetic material according to the present invention is not specifically limited, provided it contains the above-described ascorbic acid derivative as a skin-whitening active ingredient, and can be produced by a known method employed to produce ordinary cosmetic materials. The skin-whitening cosmetic material can be used not only as general-purpose skin cosmetics but as quasi drugs and external drugs, and may be provided in various forms, e.g. in the form of cream, emulsion, liquid, gel, ointment, packs, sticks or powder.

EXAMPLE 1

[Production Example 1 of Ascorbic Acid Derivative]

As will be apparent from the production steps shown by reaction formulas in FIG. 1, 2-(1,3,3-trimethyl-n-butyl)-5, 7,7-trimethyl-n-octanol, which is a branched alkanol, was reacted with phosphorus oxychloride to synthesize [2-(1,3, 3-trimethyl-n-butyl)-5,7,7-trimethyl-n-octyl] dichloro-phosphate, which is a monoalkyl dichlorophosphate. The thus synthesized substance was reacted with 5,6-O-isopropylidene-L-ascorbic acid obtained by reacting L-ascorbic acid with acetone, and the thus produced isostearyl-2-O-isopropylidene ascorbyl phosphate was hydrolyzed with hydrochloric acid, washed, isolated and purified to produce 2-(2-(1,3,3-trimethyl-n-butyl)-5,7,7-trimethyl-n-octyl)-L-ascorbyl phosphate. (In FIG. 1, the assigned numbers of peaks at $^{13}$C-NMR, which is described later, are indicated.) Now the individual synthesis steps are described in detail.

(1) Synthesis of 5,6-O-isopropylidene-L-ascorbic acid

With nitrogen substitution, 557.8 grams (9.6 moles) of acetone was cooled to −5 degrees C., 54.3 grams (0.2 moles) of 28% fuming sulfuric acid was dripped, and 176.1 grams (1.0 mole) of L-ascorbic acid was added. The mixture was then reacted at the temperature of the previous step for 17 hours, filtered and washed with cold acetone to obtain 249.5 grams of 5,6-O-isopropylidene-L-ascorbic acid (86.7% in purity) in the form of a wet cake.

(2) Synthesis of [2-(1,3,3-trimethyl-n-butyl)-5,7,7-trimethyl-n-octyl] dichlorophosphate With nitrogen substitution, 540 ml of toluene and 138.0 grams (0.9 moles) of phosphorus oxychloride were added and cooled to −10 degrees C. To this mixture, a solution of 243.5 grams (0.9 moles; 1.0 in molar ratio) of 2-(1,3,3-trimethyl-n-butyl)-5,7,7-trimethyl-n-octanol and 91.1 grams (0.9 moles) of triethylamine was dripped, and the mixture was reacted for 12 hours at 0 degrees C. The mixture was then heated to 25 degrees C., and a triethylamine hydrochloride was removed by filtering to obtain 1003.9 grams of a toluene solution of [2-(1,3,3-trimethyl-n-butyl)-5,7,7-trimethyl-n-octyl]dichlorophosphate (34.7% in concentration).

(3) Synthesis of 2-[2-(1,3,3-trimethyl-n-butyl)-5,7, 7-trimethyl-n-octyl]-L-ascorbyl phosphate With nitrogen substitution, 249.5 grams (1.0 mole) of 5,6-O-isopropylidene-L-ascorbic acid was added to 2000 ml of toluene, 202.4 grams of triethylamine was dripped at room temperature, and the mixture was stirred for one hour. Then, the mixture was cooled to −10 degrees C., and 1003.9 grams (0.9 moles) of a toluene solution of [2-(1,3,3-trimethyl-n-butyl)-5,7,7-trimethyl-n-octyl]dichlorophosphate was dripped for one hour, and the mixture was stirred at the temperature in the previous step for 14 hours. To the thus obtained reaction mass, 12312 grams of an aqueous solution of 6.7% hydrochloric acid was added, the mixture was hydrolyzed at 35 degrees C. for four hours, and the toluene layer was washed twice with 1000 grams of an aqueous solution of 10% hydrochloric acid and 7.1% sodium chloride, and further washed once with an aqueous solution of 20% sodium chloride. The toluene layer was then subjected to column chromatography, and a separated fraction thereof was subjected to vacuum concentration (35 degrees C.; 2 Torr) to remove toluene by distillation to obtain 338.9 grams of 2-[2-(1,3,3-trimethyl-n-butyl)-5,7,7-trimethyl-n-octyl]-L-ascorbyl phosphate (94.6% in purity). The yield was 66.6% (based on L-ascorbic acid).

The molecular structure of the thus obtained 2-[2-(1,3,3-trimethyl-n-butyl)-5,7,7-trimethyl-n-octyl]-L-ascorbyl phosphate was identified by infrared absorption spectrum (IR) and nuclear magnetic resonance spectrum ($^{1}$H-NMR, $^{13}$C-NMR). The results (groups or carbon atoms corresponding to the peak positions) are shown in Tables 1 to 3. It was confirmed that the thus obtained compound was an ascorbic acid derivative having the desired molecular structure, i.e. 2-[2-(1,3,3-trimethyl-n-butyl)-5,7,7-trimethyl-n-octyl]-L-ascorbyl phosphate.

TABLE 1

| IR | KBr (cm$^{-1}$) |
|---|---|
| 3370 | (OH) |
| 2954 | (CH$_2$) |
| 2904 | (CH) |
| 2867 | (CH$_2$) |
| 2715 | (P—OH) |
| 1765 | (C═O) |
| 1673 | (C═C) |
| 1473 | (CH$_3$) |
| 1216 | (P═O) |
| 1043 | (P—O—C) |

TABLE 2

| $^{1}$H-NMR | δ (ppm) from TMS in CDCl$_3$ |
|---|---|
| 1.02 | (CH$_3$-15, 24, t, 6H) |
| 1.30 | (CH$_2$-9~16, 18~23, bs, 28H) |
| 1.54 | (CH-8, bs, 1H) |
| 1.71 | (6-OH, bs, 1H) |
| 1.80 | (5-OH, bs, 1H) |
| 3.47 | (CH$_2$-7, m, 2H) |
| 3.61 | (CH$_2$-6, m, 2H) |
| 3.97 | (CH-5, m, 1H) |
| 4.76 | (CH-4, m, 1H) |

TABLE 3

| $^{13}$C-NMR | δ (ppm) from TMS in CDCl$_3$ |
|---|---|
| 169.8174 | (C-1) |
| 159.2013 | (C-3) |
| 114.209 | (C-2) |
| 77.515 | (C-4) |

TABLE 3-continued

| $^{13}$C-NMR | δ (ppm) from TMS in CDCl$_3$ |
|---|---|
| 69.4838 | (C-6) |
| 69.4265 | (C-5) |
| 63.0931 | (C-7) |
| 38.0741 | (C-8) |
| 31.2065 | (C-18) |
| 31.0443 | (C-20) |
| 30.0714 | (C-22) |
| 30.0333 | (C-11) |
| 29.9474 | (C-15) |
| 29.9093 | (C-9) |
| 29.8139 | (C-13) |
| 29.7376 | (C-12) |
| 29.6803 | (C-21) |
| 29.5563 | (C-14) |
| 29.0127 | (C-19) |
| 28.8314 | (C-10) |
| 22.6029 | (C-16) |
| 22.4789 | (C-23) |
| 18.7399 | (C-17) |
| 18.6159 | (C-24) |

EXAMPLE 2

[Production Example 2 of Ascorbic Acid Derivative]

Except that 2-(1,3,3-trimethyl-n-butyl)-5,7,7-trimethyl-n-octanol as used in Example 1 was used in the molar ratio of 2.0 based on phosphorus oxychloride, a compound was produced in exactly the same manner as in Example 1. The compound obtained was identified by infrared absorption spectrum (IR) and nuclear magnetic resonance spectrum ($^1$H-NMR, $^{13}$C-NMR). The results (groups or carbon atoms corresponding to the peak positions) are shown in Tables 4 to 6.

It was confirmed that the thus obtained compound was an ascorbic acid derivative having the desired molecular structure, i.e. 2-bis[2-(1,3,3-trimethyl-n-butyl)-5,7,7-trimethyl-n-octyl]-L-ascorbyl phosphate (91.1% in purity). The yield was 20.1% (based on L-ascorbic acid).

The molecular structure of the thus obtained compound is shown by formula [9], which includes the assigned numbers of peaks at $^{13}$C-NMR.

TABLE 4

[9]

| IR | KBr (cm$^{-1}$) | | |
|---|---|---|---|
| 3394 | (OH) | 1731 | (C=C) |
| 2955 | (CH$_2$) | 1469 | (CH$_3$) |

TABLE 4-continued

[9]

| IR | KBr (cm$^{-1}$) | | |
|---|---|---|---|
| 2905 | (CH) | 1204 | (P=O) |
| 1776 | (C=O) | 1034 | (P—O—C) |

TABLE 5

| $^1$H-NMR | δ (ppm) from TMS in CD$_3$OD |
|---|---|
| 0.90~0.95 | (CH$_3$-17, 24, 34, 41, CH$_2$-9~16, 18~23, 28~35, 37~42, bs, 40H) |
| 3.67 | (CH$_2$-7, m, 2H) |
| 3.92 | (CH-5, m, 1H) |
| 4.15 | (CH$_2$-6, m, 2H) |

TABLE 6

| $^{13}$C-NMR | δ (ppm) from TMS in CD$_3$OD |
|---|---|
| 169.8174 | (C-1) |
| 159.2013 | (C-3) |
| 114.209 | (C-2) |
| 77.515 | (C-4) |
| 69.4838 | (C-7) |
| 69.4265 | (C-5) |
| 63.0931 | (C-6) |
| 53.4022 | (C-8) |
| 48.5567 | (C-9) |
| 48.2992 | (C-11) |
| 38.0741 | (C-13) |
| 37.8547 | (C-18) |
| 37.7402 | (C-22) |
| 37.4732 | (C-16) |
| 37.4255 | (C-20) |
| 29.0127 | (C-19) |
| 28.8314 | (C-12) |
| 28.6502 | (C-21) |
| 28.5548 | (C-10) |
| 26.1321 | (C-17) |
| 25.9795 | (C-14) |
| 25.9127 | (C-23) |
| 18.7399 | (C-15) |
| 18.6159 | (C-24) |

EXAMPLE 3

[Production Example 3 of Ascorbic Acid Derivative]

Except that instead of 2-(1,3,3-trimethyl-n-butyl)-5,7,7-trimethyl-n-octanol as used in Example 1, 2-hexyldecanol was used, a compound was produced in exactly the same manner as in Example 1. The compound obtained was identified by infrared absorption spectrum (IR) and nuclear magnetic resonance spectrum ($^1$H-NMR, $^{13}$C-NMR). The results (groups or carbon atoms corresponding to the peak positions) are shown in Tables 7 to 9.

It was confirmed that the thus obtained compound was an ascorbic acid derivative having the desired molecular structure, i.e. 2-(2-hexyldecyl)-L-ascorbyl phosphate (69.7% in purity). The yield was 63% (based on L-ascorbic acid).

The molecular structure of the thus obtained compound is shown by formula [10], which includes the assigned numbers of peaks at $^{13}$C-NMR.

TABLE 7

[10]

(structure of 2-(2-hexyldecyl)-L-ascorbyl phosphate with numbered carbons)

| IR | KBr (cm$^{-1}$) | | |
|---|---|---|---|
| 3352 | (OH) | 1677 | (C=C) |
| 2956 | (CH$_2$) | 1467 | (CH$_3$) |
| 2926 | (CH) | 1219 | (P=O) |
| 2856 | (CH$_2$) | 1040 | (P—O—C) |
| 1764 | (C=O) | | |

TABLE 8

| $^1$H-NMR | δ (ppm) from TMS in CD$_3$OD |
|---|---|
| 0.89 | (CH$_3$-15, 23, t, 6H) |
| 1.10~1.33 | (CH$_2$-9~14, 16~23, bs, 26H) |
| 1.60 | (CH-8, bs, 1H) |
| 3.43 | (CH$_2$-7, d, J=5.2 Hz, 2H) |
| 3.67 | (CH$_2$-6, m, 2H) |
| 3.93 | (CH-5, m, 1H) |
| 4.90 | (CH-4, m, 1H) |

TABLE 9

| $^{13}$C-NMR | δ (ppm) from TMS in CD$_3$OD |
|---|---|
| 161.4093 | (C-1) |
| 161.3807 | (C-3) |
| — | (C-2) |
| 76.9187 | (C-4) |
| 71.6154 | (C-6) |
| 70.4708 | (C-5) |
| 63.2884 | (C-7) |
| 39.9386 | (C-8) |
| 33.0614 | (C-13) |
| 32.9756 | (C-21) |
| 31.7928 | (C-9) |
| 31.0393 | (C-16) |
| 30.7341 | (C-10) |
| 30.7055 | (C-11) |
| 30.6578 | (C-19) |
| 30.4384 | (C-12) |
| 27.9203 | (C-20) |
| 27.7295 | (C-17) |
| 27.7104 | (C-18) |
| 23.7234 | (C-14) |
| 23.7234 | (C-22) |
| 14.4331 | (C-15) |
| 14.4331 | (C-23) |

EXAMPLE 4

[Production Example 4 of Ascorbic Acid Derivative]

Except that instead of 2-(1,3,3-trimethyl-n-butyl)-5,7,7-trimethyl-n-octanol as used in Example 1, 2-octyldodecanol was used, a compound was produced in exactly the same manner as in Example 1. The compound obtained was identified by infrared absorption spectrum (IR) and nuclear magnetic resonance spectrum ($^1$H-NMR, $^{13}$C-NMR). The results (groups or carbon atoms corresponding to the peak positions) are shown in Tables 10 to 12.

It was confirmed that the thus obtained compound was an ascorbic acid derivative having the desired molecular structure, i.e. 2-(2-octyldodecyl)-L-ascorbyl phosphate (87.0% in purity). The yield was 45.4% (based on L-ascorbic acid).

The molecular structure of the thus obtained compound is shown by formula [11], which includes the assigned numbers of peaks at $^{13}$C-NMR.

TABLE 10

[11]

(structure of 2-(2-octyldodecyl)-L-ascorbyl phosphate with numbered carbons)

| IR | KBr (cm$^{-1}$) | | |
|---|---|---|---|
| 3320 | (OH) | 1662 | (C=C) |
| 2924 | (CH) | 1467 | (CH$_3$) |
| 2854 | (CH$_2$) | 1220 | (P=O) |
| 1759 | (C=O) | 1043 | (P—O—C) |

TABLE 11

| $^1$H-NMR | δ (ppm) from TMS in CD$_3$OD |
|---|---|
| 0.89 | (CH$_3$-18, 26, t, J=6.9, 6H) |
| 1.28 | (CH$_2$-9~17, 19~25, bs, 32H) |
| 1.56 | (CH-8, t, J=5.8, 1H) |
| 3.30 | (CH$_2$-7, dd, J=1.8, 3.2, 2H) |
| 3.67 | (CH$_2$-6, m, 2H) |
| 3.89 | (CH-5, m, 1H) |
| 4.87 | (CH-4, m, 1H) |

TABLE 12

| $^{13}$C-NMR | δ (ppm) from TMS in CD$_3$OD |
|---|---|
| 159.5589 | (C-1) |
| — | (C-3) |
| — | (C-2) |
| 76.7661 | (C-4) |
| 70.5853 | (C-6) |
| 70.3373 | (C-5) |
| 63.3933 | (C-7) |
| 39.9386 | (C-8) |
| 33.0805 | (C-16) |
| 33.0805 | (C-24) |
| 31.9359 | (C-9) |
| 31.9073 | (C-19) |
| 31.1061 | (C-10) |
| 31.0775 | (C-11) |
| 30.7627 | (C-12) |

TABLE 12-continued

| $^{13}$C-NMR | δ (ppm) from TMS in CD$_3$OD |
|---|---|
| 30.6864 | (C-13) |
| 30.6864 | (C-14) |
| 30.4765 | (C-15) |
| 30.4765 | (C-22) |
| 27.8153 | (C-23) |
| 27.7963 | (C-20) |
| 27.7295 | (C-21) |
| 23.7329 | (C-17) |
| 23.7329 | (C-25) |
| 14.4521 | (C-18) |
| 14.4521 | (C-26) |

EXAMPLE 5

[Production Example 5 of Ascorbic Acid Derivative]

A sodium salt of 2-(2-heptylundecyl)-L-ascorbyl phosphate was produced as follows.

With nitrogen substitution, 249.5 grams (1.0 mole) of 5,6-O-isopropylidene-L-ascorbic acid was added to 2000 ml of toluene, 202.4 grams of triethylamine was dripped at room temperature, and the mixture was stirred for one hour. Then, the mixture was cooled to −10 degrees C., and 1003.9 grams (0.9 moles) of a toluene solution of (2-heptylundecyl) dichlorophosphate was dripped for one hour, and the mixture was stirred at the temperature in the previous step for 14 hours. To the thus obtained reaction mass, 12312 grams of an aqueous solution of 6.7% hydrochloric acid was added, the mixture was hydrolyzed at 35 degrees C. for four hours, and the toluene layer was washed twice with 1000 grams of an aqueous solution of 10% hydrochloric acid and 7.1% sodium chloride, and further washed once with an aqueous solution of 20% sodium chloride.

Then, an aqueous solution of 30% NaOH was added to the toluene layer thereof to adjust the pH value to 7. Ethanol was then added to the separated aqueous layer thereof, the mixture thereof was subjected to vacuum concentration to remove water and ethanol by distillation, and the thus deposited crystal was filtered and dried to obtain 344.9 grams of a sodium salt of 2-(2-heptylundecyl)-L-ascorbyl phosphate (92.3% in purity). The yield was 60.0% (based on L-ascorbic acid).

The molecular structure of the thus obtained compound was identified by infrared absorption spectrum (IR) and nuclear magnetic resonance spectrum ($^1$H-NMR, $^{13}$C-NMR). It was confirmed that the thus obtained compound was an ascorbic acid derivative having the desired molecular structure, i.e. a sodium salt of 2-(2-heptylundecyl)-L-ascorbyl phosphate. Identification based on the results of peak positions and the corresponding groups and carbon atoms were made in the same manner as in Example 1, so that its detailed description is omitted.

EXAMPLE 6

[Production Example 6 of Ascorbic Acid Derivative]

Figure 2:
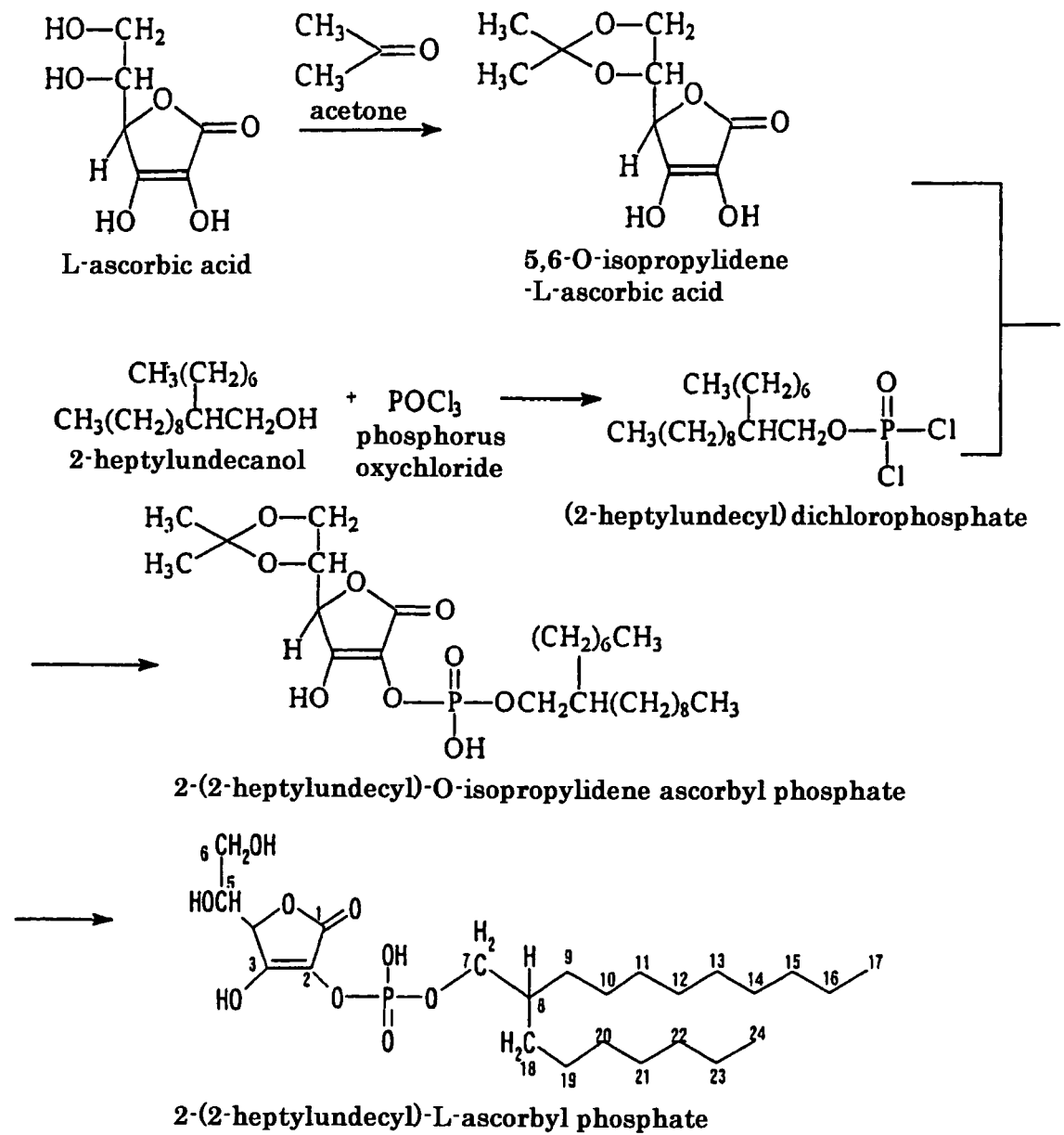
FIG. 2 shows the process for producing the ascorbic acid derivative of Example 6, using reaction formulas.

As will be apparent from the production steps shown by reaction formulas in FIG. 2, 2-heptylundecanol, which is a branched alkanol, was reacted with phosphorus oxychloride to synthesize (2-heptylundecyl)dichlorophosphate, which is a monoalkyl dichlorophosphate. The thus synthesized substance was reacted with 5,6-O-isopropylidene-L-ascorbic acid obtained by reacting L-ascorbic acid with acetone, and the thus produced isostearyl-2-O-isopropylidene ascorbyl phosphate was hydrolyzed with hydrochloric acid, washed, isolated and purified to produce 2-(2-heptylundecyl)-L-ascorbyl phosphate. (In FIG. 2, the assigned numbers of peaks at $^{13}$C-NMR, which is described later, are indicated.) Now the individual synthesis steps are described in detail.

(1) Synthesis of 5,6-O-isopropylidene-L-ascorbic acid

With nitrogen substitution, 557.8 grams (9.6 moles) of acetone was cooled to −5 degrees C., 54.3 grams (0.2 moles) of 28% fuming sulfuric acid was dripped, and 176.1 grams (1.0 mole) of L-ascorbic acid was added. The mixture was then reacted at the temperature of the previous step for 17 hours, filtered and washed with cold acetone to obtain 249.5 grams of 5,6-O-isopropylidene-L-ascorbic acid (86.7% in purity) in the form of a wet cake.

(2) Synthesis of (2-heptylundecyl)dichlorophosphate

With nitrogen substitution, 540 ml of toluene and 138.0 grams (0.9 moles) of phosphorus oxychloride were added and cooled to −10 degrees C. To this mixture, a solution of 243.5 grams (0.9 moles; 1.0 in molar ratio) of 2-heptylundecanol and 91.1 grams (0.9 moles) of triethylamine was dripped, and the mixture was reacted for 12 hours at 0 degrees C. The mixture was then heated to 25 degrees C., and a triethylamine hydrochloride was removed by filtering to obtain 1003.9 grams of a toluene solution of (2-heptylundecyl)dichlorophosphate (34.7% in concentration).

(3) Synthesis of 2-(2-heptylundecyl)-L-ascorbyl phosphate

With nitrogen substitution, 249.5 grams (1.0 mole) of 5,6-O-isopropylidene-L-ascorbic acid was added to 2000 ml of toluene, 202.4 grams of triethylamine was dripped at room temperature, and the mixture was stirred for one hour. Then, the mixture was cooled to −10 degrees C., and 1003.9 grams (0.9 moles) of a toluene solution of (2-heptylundecyl) dichlorophosphate was dripped for one hour, and the mixture was stirred at the temperature in the previous step for 14 hours. To the thus obtained reaction mass, 12312 grams of an aqueous solution of 6.7% hydrochloric acid was added, the mixture was hydrolyzed at 35 degrees C. for four hours, and the toluene layer was washed twice with 1000 grams of an aqueous solution of 10% hydrochloric acid and 7.1% sodium chloride, and further washed once with an aqueous solution of 20% sodium chloride. The toluene layer was then subjected to column chromatography, and a separated fraction thereof was subjected to vacuum concentration (35 degrees C.; 2 Torr) to remove toluene by distillation to obtain 338.9 grams of 2-(2-heptylundecyl)-L-ascorbyl phosphate (94.6% in purity). The yield was 66.6% (based on L-ascorbic acid).

The molecular structure of the thus obtained 2-(2-heptylundecyl)-L-ascorbyl phosphate was identified by infrared absorption spectrum (IR) and nuclear magnetic resonance spectrum ($^1$H-NMR, $^{13}$C-NMR). It was confirmed that the thus obtained compound was an ascorbic acid derivative having the molecular structure of formula [12], i.e. 2-(2-heptylundecyl)-L-ascorbyl phosphate.

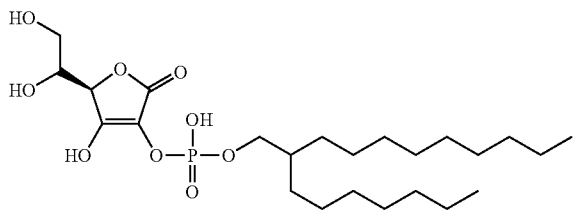

EXAMPLE 7

[Production Example 7 of Ascorbic Acid Derivative]

Except that 2-heptylundecanol as used in Example 6 was used in the molar ratio of 2.0 based on phosphorus oxychloride, a compound was produced in exactly the same manner as in Example 1. The compound obtained was identified by infrared absorption spectrum (IR) and nuclear magnetic resonance spectrum ($^1$H-NMR, $^{13}$C-NMR). From these results (groups or carbon atoms corresponding to the peak positions), it was confirmed that the thus obtained compound was an ascorbic acid derivative having the desired molecular structure, i.e. 2-bis(2-heptylundecyl)-L-ascorbyl phosphate (91.1% in purity). The yield was 20.1% (based on L-ascorbic acid).

temperature in the previous step for 14 hours. To the thus obtained reaction mass, 12312 grams of an aqueous solution of 6.7% hydrochloric acid was added, the mixture was hydrolyzed at 35 degrees C. for four hours, and the toluene layer was washed twice with 1000 grams of an aqueous solution of 10% hydrochloric acid and 7.1% sodium chloride, and further washed once with an aqueous solution of 20% sodium chloride.

Then, an aqueous solution of 30% NaOH was added to the toluene layer thereof to adjust the pH value to 7. Ethanol was then added to the separated aqueous layer thereof, the mixture thereof was subjected to vacuum concentration to remove water and ethanol by distillation, and the thus deposited crystal was filtered and dried to obtain 344.9 grams of a sodium salt of 2-[2-(1,3,3-trimethyl-n-butyl)-5,7,7-trimethyl-n-octyl]-L-ascorbyl phosphate (92.3% in purity). The yield was 60.0% (based on L-ascorbic acid).

The molecular structure of the thus obtained compound was identified by infrared absorption spectrum (IR) and nuclear magnetic resonance spectrum ($^1$H-NMR, $^{13}$C-NMR). It was confirmed that the thus obtained compound was an ascorbic acid derivative having the desired molecular structure, i.e. a sodium salt of 2-[2-(1,3,3-trimethyl-n-butyl)-5,7,7-trimethyl-n-octyl]-L-ascorbyl phosphate.

Using the ascorbic acid derivatives obtained in Production Examples 1, 3 and 4 as active ingredients, the cosmetic materials (lotions) of Examples 8 to 12 were prepared. The contents of components forming each ascorbic acid derivative are shown in Table 13.

TABLE 13

|  | Example of the invention | | | | | Comparative Example | |
|---|---|---|---|---|---|---|---|
|  | 8 | 9 | 10 | 11 | 12 | 1 | 2 |
| 2-[2-(1,3,3-trimethyl-n-butyl)-5,7,7-trimethyl-n-octyl]-L-ascorbyl phosphate | 0.05 | 0.5 | 5.0 | — | — | 0.01 | — |
| 2-(2-hexyldecyl)-L-ascorbyl phosphate | — | — | — | 10.0 | — | — | — |
| 2-bis(2-octyldodecyl)-L-ascorbyl phosphate | — | — | — | — | 10.0 | — | — |
| L-ascorbyl-2-glucoside | — | — | — | — | — | — | 2.0 |
| sodium hydroxide | — | — | — | 0.2 | 0.2 | — | 0.05 |
| ethanol | 5.0 | 5.0 | 5.0 | 5.0 | 5.0 | 5.0 | 5.0 |
| glycerin | 10.0 | 10.0 | 10.0 | 10.0 | 10.0 | 10.0 | 10.0 |
| POE hydrogenated castor oil | 0.5 | 0.5 | 0.5 | 0.5 | 0.5 | 0.5 | 0.5 |
| purified water | balance | balance | balance | balance | balance | balance | balance |

EXAMPLE 8

[Production Example 8 of Ascorbic Acid Derivative]

A sodium salt of 2-[2-(1,3,3-trimethyl-n-butyl)-5,7,7-trimethyl-n-octyl]-L-ascorbyl phosphate was produced as follows.

With nitrogen substitution, 249.5 grams (1.0 mole) of 5,6-O-isopropylidene-L-ascorbic acid was added to 2000 ml of toluene, 202.4 grams of triethylamine was dripped at room temperature, and the mixture was stirred for one hour. Then, the mixture was cooled to −10 degrees C., and 1003.9 grams (0.9 moles) of a toluene solution of [2-(1,3,3-trimethyl-n-butyl)-5,7,7-trimethyl-n-octyl]dichlorophosphate was dripped for one hour, and the mixture was stirred at the

[Determination of the Skin-Whitening Effect]

For three months, every night and morning, each cosmetic material was used by every member of one of a plurality of groups of subjects (each group consisting of 20 subjects) who are suffering from spots, freckles or darkened skin. At the end of the three-month period, the individual subjects made evaluations for the effects of the cosmetic materials they used by selecting one of the following four categories.

Markedly effective: Pigmentation is barely recognizable.

Effective: Pigmentation has improved.

Slightly effective: Pigmentation has slightly improved.

Ineffective: No improvement in pigmentation has been observed.

Table 14 shows the results of evaluations, in which symbol ⊙ means that not less than 80% of the subjects evaluated the cosmetic material they used as markedly effective or effective;
symbol ○ means that not less than 60% and less than 80% of the subjects evaluated the cosmetic material they used as markedly effective or effective;
symbol Δ means that not less than 40% and less than 60% of the subjects evaluated the cosmetic material they used as markedly effective or effective; and
symbol X means that less than 40% of the subjects evaluated the cosmetic material they used as markedly effective or effective.

TABLE 14

|  | Example of the invention | | | | | Comparative Example | |
|---|---|---|---|---|---|---|---|
|  | 8 | 9 | 10 | 11 | 12 | 1 | 2 |
| Skin-whitening effect after continuously applying cosmetic material | Δ | ○ | ⊙ | ⊙ | ⊙ | X | Δ |

As will be apparent from Table 14, at least 40% of the subjects who used any of Examples 8 to 12, which contains a predetermined amount (not less than 0.05 percent by weight) of L-ascorbic acid-2-phosphate ester, felt that they were markedly effective or effective. Also, more than 60% and more than 80% of the subjects who used Examples 9 and Examples 10 to 12, respectively, evaluated the respective cosmetic materials as markedly effective or effective. Thus, it was confirmed that the skin-whitening cosmetic material according to the present invention exhibits physiological activities that are inherent to L-ascorbic acid and beneficial in whitening the skin.

The following are the composition of typical cosmetic materials containing L-ascorbic acid-2-phosphate ester as their active ingredient. The numerical values on the right column are the contents (percent by weight) of the respective components.

EXAMPLE 13

Gel Cream

| 2-(2-heptylundecyl)-L-ascorbyl phosphate | 5.0 |
|---|---|
| glycerin | 10.0 |
| ethanol | 5.0 |
| sodium hydroxide | 0.5 |
| carboxyvinyl polymer | 0.8 |
| perfume | adequate quantity |
| preservative | adequate quantity |
| purified water | balance |

EXAMPLE 14

Emulsion

| 2-(2-hexyldecyl)-L-ascorbyl phosphate | 10.0 |
|---|---|
| 1,3-butylene glycol | 10.0 |
| carboxyvinyl polymer | 0.3 |
| squalane | 5.0 |
| cetanol | 0.8 |

-continued

| L-arginine | 0.3 |
|---|---|
| perfume | adequate quantity |
| preservative | adequate quantity |
| purified water | balance |

EXAMPLE 15

Cream

| 2-bis(2-octyldodecyl)-L-ascorbyl phosphate | 10.0 |
|---|---|
| 1,3-butylene glycol | 10.0 |
| carboxyvinyl polymer | 0.3 |
| squalane | 5.0 |
| cetanol | 2.0 |
| beeswax | 3.0 |
| L-arginine | 0.3 |
| perfume | adequate quantity |
| preservative | adequate quantity |
| purified water | balance |

What is claimed is:

1. An ascorbic acid derivative comprising an L-ascorbic acid-2-phosphate ester or a salt thereof,
   wherein the phosphate ester has a branched alkyl group which is branched at position 2,
   wherein the L-ascorbic acid-2-phosphate ester is represented by formula [1],

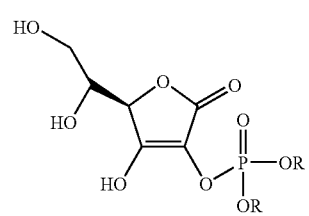

[1]

wherein R is a hydrogen (H) atom or an alkyl group branched at position 2 and including 4 to 30 carbon atoms, but both R groups are not hydrogen (H) atoms, and
   wherein said branched alkyl group is 2-heptylundecyl group, 2-octyldecyl group, 2-octyldodecyl group, 2-hexyldecyl group, 2-hexyldodecyl group, 2-isoheptylisoundecyl group or 2-(1,3,3-trimethyl-n-butyl)-5,7,7-trimethyl-n-octyl group.

2. The ascorbic acid derivative of claim 1, comprising a salt selected from the group consisting of a sodium salt, a potassium salt, a magnesium salt and a calcium salt of the L-ascorbic acid-2-phosphate ester.

3. A process for producing the ascorbic acid derivative of claim 1, said process comprising reacting a branched alkanol represented by formula [2],

R—OH         [2]

wherein R is an alkyl group branched at position 2 and including 4 to 30 carbon atoms, with phosphorus oxychloride to synthesize monoalkyldi-chiorophosphate represented by formula [3],

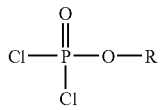
[3]

wherein R is an alkyl group branched at position 2 and including 4 to 30 carbon atoms,
or dialkylmonochlorophosphate represented by formula [4],

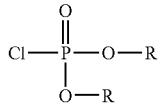
[4]

wherein R is an alkyl group branched at position 2 and including 4 to 30 carbon atoms,
reacting the thus obtained substance with 5,6-O-isopropylidene-L-ascorbic acid obtained by reacting L-ascorbic acid with acetone, and
subjecting the thus obtained substance to acid hydrolysis.

4. A process for producing the ascorbic acid derivative of claim 2, said process comprising reacting a branched alkanol represented by formula [2],

R—OH  [2]

wherein R is an alkyl group branched at position 2 and including 4 to 30 carbon atoms,
with phosphorus oxychloride to synthesize monoalkyldichlorophosphate represented by formula [3],

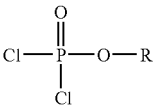
[3]

wherein R is an alkyl group branched at position 2 and including 4 to 30 carbon atoms,
reacting the thus obtained substance with 5,6-O-isopropylidene-L-ascorbic acid obtained by reacting L-ascorbic acid with acetone, and
subjecting the thus obtained substance to acid hydrolysis.

* * * * *